United States Patent [19]

Eberle et al.

[11] 4,325,867

[45] Apr. 20, 1982

[54] PROCESS FOR THE RECOVERY OF α-2-SB-GLYCOPROTEIN

[75] Inventors: Walter Eberle, Bernried; Winfried Albert, Pähl, both of Fed. Rep. of Germany

[73] Assignee: Boehringer Mannheim GmbH, Mannheim-Waldhof, Fed. Rep. of Germany

[21] Appl. No.: 208,759

[22] Filed: Nov. 20, 1980

[30] Foreign Application Priority Data

Dec. 7, 1979 [DE] Fed. Rep. of Germany ....... 2949407

[51] Int. Cl.³ ................................................ C07G 7/00
[52] U.S. Cl. ............................ 260/112 B; 260/112 R; 260/117; 260/123.7; 424/85; 424/101; 424/177
[58] Field of Search ............... 260/112 R, 112 B, 177, 260/123.7

[56] References Cited

U.S. PATENT DOCUMENTS 4,104,266 8/1978 Wickerhauser ................. 260/112 B
4,278,594 7/1981 Amrani ........................... 260/112 B

OTHER PUBLICATIONS

Journal of Biological Chemistry, vol. 245, No. 21, 1970, pp. 5728–5736, Mosesson et al.
Journal of Biological Chemistry, vol. 250, No. 16, 1975, pp. 6614–6621, Mosher.
Biochemical J. (1978), 175, 333–336, Vuento et al.
Annals of N.Y. Academy of Sciences, vol. 312 (1978), 178–191, Ruoslahti et al.
Biochem. J. (1978), 169, 55–59, Dessau et al.
Science, vol. 201, Aug. 1978, pp. 622–624, Saba et al.
Nature, vol.–275, 1978, pp. 179–184, Yamada et al.

*Primary Examiner*—Howard E. Schain
*Attorney, Agent, or Firm*—Sprung, Felfe, Horn, Lynch & Kramer

[57] ABSTRACT

The present invention provides a process for obtaining α-2-SB-glycoprotein from physiological solutions thereof by binding to a bindable protein immobilized on an insoluble carrier, wherein the carrier-fixed protein is subsequently washed with a buffer solution of pH 6 to 8.5 and thereafter the α-2-SB-glycoprotein is eluted with a buffer solution with a pH of 9 or more and isolated from the eluate.

12 Claims, No Drawings

PROCESS FOR THE RECOVERY OF α-2-SB-GLYCOPROTEIN

This invention relates to a process for obtaining alpha-2-SB-glycoprotein, which is also known as fibronectin, cold-insoluble protein and LETS protein, from physiological solutions thereof, for example, plasma, serum, blood or organ stroma.

α-2-SB-glycoprotein is a substance which is present in blood and organ stroma. The serum protein has the electrophoretic motility of an α2-globulin and a sedimentation coefficient of 12 to 14 S. Its molecular weight is about 400,000 to 440,000. It consists of two sub-units which are connected by disulphide bridges. The concentration thereof in the plasma of healthy subjects is 300 to 500 μg./ml. A more detailed description thereof is given in Nature, 275, 179/1978.

α-2-SB-glycoprotein is a substrate of activated coagulation factor XIII, i.e. of Factor XIIIa (plasma transglutaminase or fibrinoligase). It is binding to fibrinogen and fibrin, especially in the cold. Since it can react with fibrin during coagulation, lower concentrations are usually found in serum than in plasma. Affinities towards gelatine and collagen have also been ascribed to α-2-SB-glycoprotein.

The form of the α2-SB-glycoprotein bound to the cell membrane is present in the case of variously transformed cells in substantially lower density. The altered phenotype of these cells can, to a certain extent, be corrected by the adsorption of an α-2-SB-glycoprotein on the cell membranes, for example again producing the adhesion on to culture vessels, contact inhibition and the like.

One physiological property of α-2-SB-glycoprotein is its non-immunological, opsonizing action. Thus, for example, the take up of particulate material by the reticuloendothial system (RES) is promoted. A direct correlation is postulated between the α-2-SB-glycoprotein level in the plasma and the activity of the RES.

In the case of certain diseases in which intravascular coagulation disturbances occur, there is increased utilization of α-2-SB-glycoprotein, the latter thereby being consumed as a non-specific opsonin. Thus, in the course of certain diseases, the α-2-SB-glycoprotein level can change. For example, increased values occur in diseases of the connective tissues. In the case of metastazing tumours, increased values are frequently observed in the advanced stages.

It is assumed that the removal of damaged autologous tissue and of circulating components, for example soluble fibrin, by non-immunological opsonization is an important physiological process. For this reason, a considerable decrease of α-2-SB-glycoprotein can lead to loss of organ function in cases of seriously ill patients. By means of the infusion of α-2-SB-glycoprotein, a positive effect could be achieved on the state of patients with intravascular coagulation disturbances, for example in the case of severe infections (sepsis), in the case of tumors, severe injuries and after operations (see Science, 201, 622/1978).

However, a prerequisite for a directed therapy is the sufficient availability of α-2-SB-glycoprotein.

The affinity chromatography of α-2-SB-glycoprotein on Sepharose-bound gelatine was used by Ruoslahti and Engvall (see Ann. of the New York Academy of Sciences, 312, 186/1978) for the isolation of this protein. The protein could be eluted by means of urea, sodium thiocyanate, sodium iodide, ethylene glycol, specific antibodies or by the action of collagenase upon the gelatine-containing affinity matrix. According to Biochem. J., 175, 333/1978, various cationic compounds, for example arginine, spermidine, putrescine and the like, can be used to elute this protein from gelatine-Sepharose. However, these methods suffer from certain disadvantages: thus, for example, in the case of elution with chaotropic substances, a dialysis must subsequently be carried out. After removal of these substances, aggregation phenomena then occur when the concentration of α-2-SB-glycoprotein exceeds 1 mg./ml. Thus, a material prepared in this manner can only be infused with difficulty. In the case of elution with cationic substances, it was observed that the haemagglutination activity of α-2-SB-glycoprotein was inhibited.

Furthermore, our own investigations have shown that the immunological properties of α-2-SB-glycoprotein are diminished after isolation by means of cationic substances. In Biochem. J., 169, 55/1978, a process is described in which α-2-SB-glycoprotein can be eluted by the addition of 1 mol/liter potassium bromide. However, this process suffers from the same disadvantages as the above-mentioned methods.

It is, therefore, an object of the present invention to provide a process which makes possible a simple enrichment or isolation of α-2-SB-glycoprotein without losses in the immunological and physiological activity thereby occurring.

Thus, according to the present invention, there is provided a process for obtaining α-2-SB-glycoprotein from physiological solutions thereof by binding to a bindable protein immobilized on an insoluble carrier, wherein the carrier-fixed protein is subsequently washed with a buffer solution of pH 6 to 8.5, and thereafter the α-2-SB-glycoprotein is eluted with a buffer solution with a pH of 9 or more and isolated from the eluate.

Thus, we have, surprisingly, found that under the pH conditions used according to the process of the present invention, the pure protein can be simply obtained without changing its properties and especially without aggregation.

The bindable protein used can be gelatin collagen and/or fibrin but other bindable proteins can also be used. The carrier for the bindable protein can be any carrier material conventionally used for immobilizing proteins, preferred carriers being those based on carbohydrates, for example cellulose, agarose and the like. However, other hydrophilic organic and inorganic carrier substances can also be used, typical examples thereof including polymeric derivatives of acrylic acid and methacrylic acid, which can carry polar substituents, such as hydroxyl groups, amino groups and the like.

The nature of the binding of the bindable protein on to the carrier is not of importance so long as it makes it impossible to wash out the immobilized, bindable protein from the carrier under the process conditions. Covalently fixed proteins are preferred. Many processes are known for the covalent carrier-fixing of proteins and do not need to be explained here in detail. Fixing can, for example, take place by activation of the carrier, for example cyanogen bromide activation of carbohydrates, or by activation of the protein or by means of difunctional bridge-building substances.

The physiological α-2-SB-glycoprotein solution is contacted with the immobilized, bindable protein and left in contact therewith until all of the α-2-SB-glycoprotein is bound to the carrier. This usually requires about 0.5 to 2 hours. During the contacting, it is preferable to stir. However, the period of contacting can be greater or smaller, depending upon the nature of the physiological solution, its pre-treatment, for example citrate plasma or EDTA-plasma (EDTA=ethylene-diamine-tetraacetic acid), the nature of the carrier-fixed, bindable protein and of the carrier. Furthermore, the period of contacting depends upon the ratio of the amount of the immobilized, bindable protein used and of the protein present in the solution.

After ending the contacting or incubation, the main amount of the protein originally present in the solution is washed out with a buffer solution of pH 6 to 8.5. The pH range of from 7 to 8 is especially suitable and the best results are obtained at a pH of from 7.3 to 7.7. The buffer concentration can be varied within wide limits. In general, good results are obtained at concentrations of from about 0.01 to about 0.3 mol/liter. A neutral salt is preferably added to the buffer solution to increase the ion strength. If such a salt is employed, then its concentration is preferably from 0.5 to 2 mol/liter. Examples of neutral salts which can be used include the alkali metal chlorides, such as sodium chloride, potassium chloride, lithium chloride and the like, which are preferred. However, other salts of strong bases with strong acids can also be used. Washing of the carrier substance is carried out until no more protein can be washed out under the stated pH conditions.

The α-2-SB-glycoprotein is subsequently eluted from the carrier with the help of a buffer solution with a pH of 9 or more and preferably of 10 to 12, the best results being achieved at pH values of from 10.5 to 11.5. The solution of α-2-SB-glycoprotein thus obtained, which is practically free of foreign protein, can, after removal of the buffer substance by dialysis, be reduced to dryness, for example by lyophilization or evaporation. According to a preferred embodiment of the process of the present invention, a volatile buffer substance is used for the elution so that the eluate obtained can, without previous dialysis, be directly lyophilized.

According to the present invention, buffer substances can generally be used which are able to buffer in the stated pH range. Typical examples of suitable non-volatile buffers include tris-hydrochloric acid buffer, borate buffer, veronal buffer, glycine/aqueous sodium hydroxide buffer and carbonate buffer and examples of volatile buffers include triethylammonium bicarbonate buffer, ammonium bicarbonate/carbon dioxide buffer, ammonium carbonate buffer, collidine acetate buffer, pyridinium acetate buffer and cyclohexylaminopropane-sulphonate buffer.

The process according to the present invention is simple to carry out and enables pure α-2-SB-glycoprotein to be obtained, the immunological activity and binding properties of which remain unchanged. Because of the known adhesive-like properties of α-2-SB-glycoprotein, it is very surprising that it can be bound to an insoluble carrier and can again be eluted therefrom under mild conditions, without aggregation occurring.

The following Example is given for the purpose of illustrating the present invention:

EXAMPLE

On to cyanogen bromide-activated Sepharose (commercial product of Pharmacia), there is covalently bound 1 mg. gelatine/ml. Sepharose according to the directions of the producer. 20 litters of human plasma are mixed with 10 liters of gelatine-Sepharose and incubated, with stirring, for a period of 2 hours.

Subsequently, the Sepharose is washed over a glass frit with 0.05 mol/liter tris-hydrochloric acid buffer (pN 7.5) which contains 1 mol sodium chloride/liter until no more protein can be detected in the wash solution.

The bound α-2-SB-glycoprotein is subsequently eluted with 0.05 mol/liter cyclohexylaminopropane-sulphonic acid which has been adjusted to a pH of 11.0 by the addition of 1 mol/liter of aqueous sodium hydroxide solution. The total yield is 4 g. α-2-SB-glycoprotein.

The protein obtained is immune-electrophoretically pure α-2-SB-glycoprotein. After the elution, this protein shows complete immunological activity and its binding property to the affinity absorbents after neutralization is retained.

It will be understood that the specification and examples are illustrative but not limitative of the present invention and that other embodiments within the spirit and scope of the invention will suggest themselves to those skilled in the art.

What is claimed is:

1. Process for obtaining alpha-2-SB-glycoprotein from physiological solutions thereof, which process comprises binding the alpha-2-SB-glycoprotein to a bindable protein immobilized on an insoluble carrier, washing the carrier-bound protein with a buffer solution of pH 6 to 8.5, and eluting the alpha-2-SB-glycoprotein with a buffer solution of pH 9 or more, and isolating same from the eluate.

2. Process as claimed in claim 1 wherein the bindable protein used is gelatin.

3. Process as claimed in claim 1 wherein the bindable protein used is collagen.

4. Process as claimed in claim 1 wherein the bindable protein used is fibrin.

5. Process as claimed in claim 1 wherein said carrier is based on a carbohydrate.

6. Process as claimed in claim 1 wherein the bindable protein is covalently fixed onto said carrier.

7. Process as claimed in claim 1 wherein the carrier-bound protein is washed with 0.01 to 0.3 moles per liter buffer of pH 7 to 8.

8. Process as claimed in claim 7 wherein said buffer contains 0.5 to 2 moles per liter of neutral salt.

9. Process as claimed in claim 8 wherein the neutral salt is an alkali metal chloride.

10. Process as claimed in claim 1 wherein elution is carried out with a buffer with a pH of 10 to 12.

11. Process as claimed in claim 1 wherein elution is carried out with a volatile buffer substance.

12. Process as claimed in claim 11 wherein the eluate obtained is directly lyophilized.

* * * * *